(12) United States Patent
Aoyagi

(10) Patent No.: US 11,195,272 B2
(45) Date of Patent: Dec. 7, 2021

(54) MEDICAL IMAGE PROCESSING APPARATUS, MEDICAL IMAGE PROCESSING SYSTEM, AND MEDICAL IMAGE PROCESSING METHOD

(71) Applicant: CANON MEDICAL SYSTEMS CORPORATION, Otawara (JP)

(72) Inventor: Kota Aoyagi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 149 days.

(21) Appl. No.: 16/541,248

(22) Filed: Aug. 15, 2019

(65) Prior Publication Data

US 2020/0065963 A1      Feb. 27, 2020

(30) Foreign Application Priority Data

Aug. 21, 2018   (JP) .............................. JP2018-154776
Jul. 5, 2019    (JP) .............................. JP2019-126353

(51) Int. Cl.
  *G06T 7/00*      (2017.01)
  *A61B 6/03*      (2006.01)
  (Continued)

(52) U.S. Cl.
  CPC ............ *G06T 7/0012* (2013.01); *A61B 5/055* (2013.01); *A61B 6/032* (2013.01); *G06T 5/50* (2013.01);
  (Continued)

(58) Field of Classification Search
  CPC ......... G06T 7/0012; G06T 2207/10081; G06T 5/50; G06T 2207/10088; G06T 2210/41;
  (Continued)

(56) References Cited

U.S. PATENT DOCUMENTS

2010/0296715 A1 *  11/2010  Kinosada ............... A61B 5/418
                                                 382/131
2013/0004043 A1 *  1/2013  Ross ....................... G06T 7/136
                                                 382/131

(Continued)

FOREIGN PATENT DOCUMENTS

WO    WO 2012/151579 A2    11/2012

OTHER PUBLICATIONS

Uchiyama Y, et al. "Quantitative computerized analysis of diffuse lung disease in high-resolution computed tomography " Med Phys. AAPM; 2003;30(9) pp. 2440-2454.

(Continued)

*Primary Examiner* — Emily C Terrell
*Assistant Examiner* — Molly Delaney
(74) *Attorney, Agent, or Firm* — Oblon, McClelland, Maier & Neustadt, L.L.P.

(57) ABSTRACT

In one embodiment, a medical image processing apparatus includes a memory storing a predetermined program and processing circuitry. The processing circuitry is configured, by executing the predetermined program, to acquire a plurality of images that are obtained by imaging a same object and are different in imaging time, classify tissue property of the object into a plurality of tissue-property classes by analyzing the tissue property of the object based on pixel values of respective regions of the plurality of images, assign the classified tissue-property classes to the respective regions of the plurality of images, and estimate change in (Continued)

disease state of the object from change in the classified tissue-property classes in respectively corresponding regions of the plurality of images.

14 Claims, 16 Drawing Sheets

(51) Int. Cl.
    *A61B 5/055*     (2006.01)
    *G06T 5/50*     (2006.01)
    *G06T 7/11*     (2017.01)

(52) U.S. Cl.
    CPC ....... *G06T 7/11* (2017.01); *G06T 2207/10081* (2013.01); *G06T 2207/10088* (2013.01); *G06T 2207/20216* (2013.01); *G06T 2207/30061* (2013.01); *G06T 2207/30096* (2013.01); *G06T 2210/41* (2013.01)

(58) Field of Classification Search
    CPC . G06T 2207/30061; G06T 2207/20216; G06T 2207/30096; G06T 7/11; A61B 6/032; A61B 5/055; A61B 5/7275; A61B 6/5217; A61B 6/50; G16H 50/30
    See application file for complete search history.

(56) References Cited

U.S. PATENT DOCUMENTS

| | | | | |
|---|---|---|---|---|
| 2013/0136325 | A1* | 5/2013 | Sakamoto | G06K 9/00147 382/128 |
| 2013/0208970 | A1* | 8/2013 | Fujisawa | A61B 6/507 382/131 |
| 2014/0184608 | A1* | 7/2014 | Robb | A61B 6/5217 345/440 |
| 2015/0356730 | A1* | 12/2015 | Grove | G06T 7/64 382/124 |
| 2017/0024884 | A1* | 1/2017 | Ishihara | A61B 6/461 |
| 2017/0151226 | A1* | 6/2017 | Bayever | A61K 9/0019 |
| 2018/0046750 | A1* | 2/2018 | Korn | G16B 5/00 |
| 2018/0247410 | A1* | 8/2018 | Madabhushi | G06T 7/11 |
| 2018/0253841 | A1* | 9/2018 | Madabhushi | G06T 7/155 |
| 2019/0019300 | A1* | 1/2019 | Simpson | G16H 30/20 |
| 2019/0266725 | A1* | 8/2019 | Zalev | G06T 7/0012 |

OTHER PUBLICATIONS

Bartholmai, B, et al. "Quantitative CT Imaging of Interstitial Lung Diseases", NIH Public Access, J Thorac Imaging, Sep. 2013; 28(5); pp. 1-21.

* cited by examiner

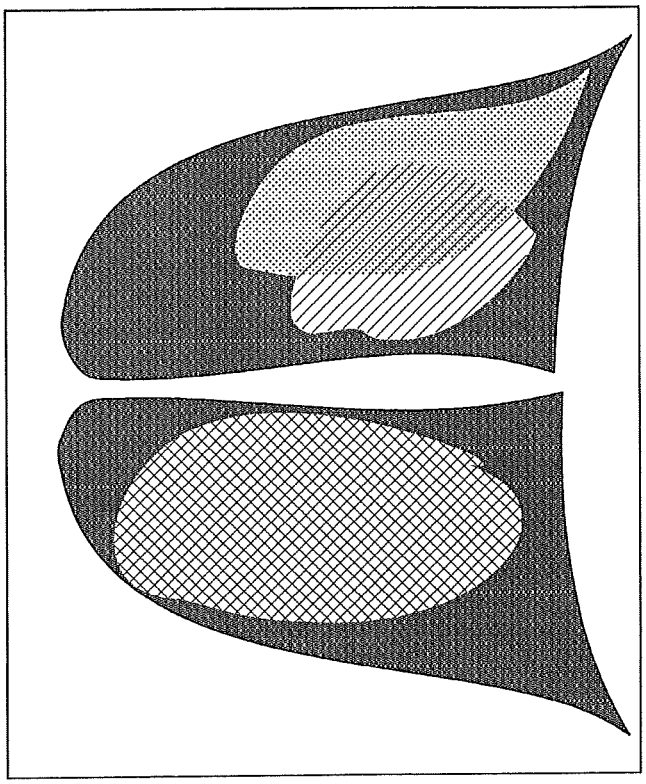
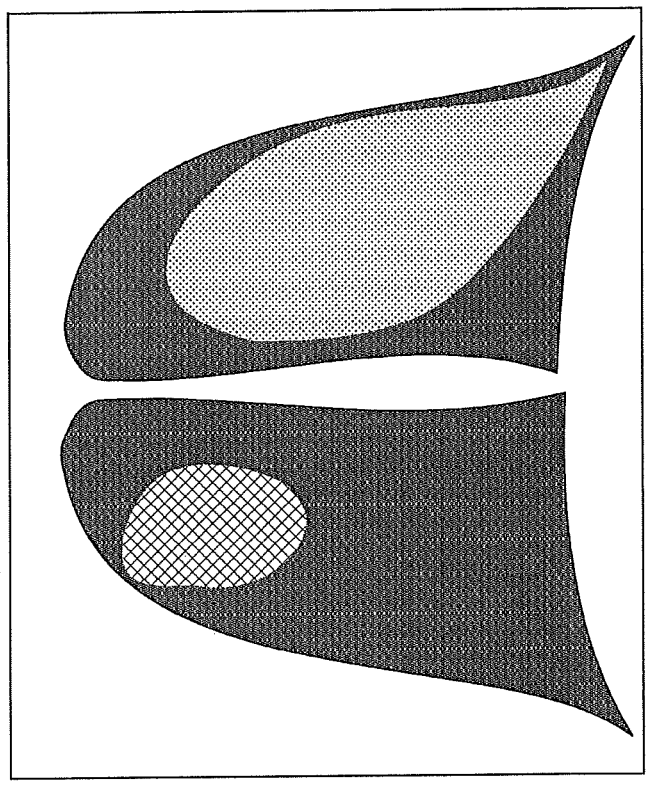
FIG. 4

TYPES OF TEXTURE PATTERNS
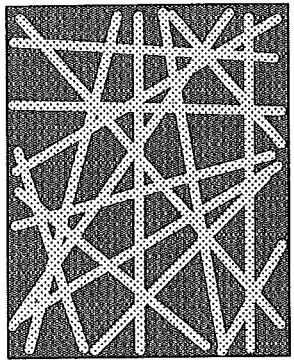
TYPE A
(NORMAL)
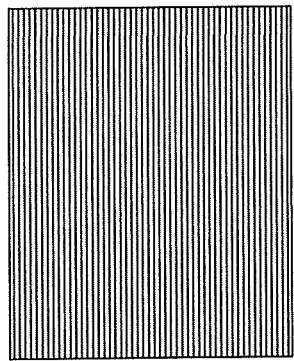
TYPE B
(GROUND-GLASS OPACITIES)
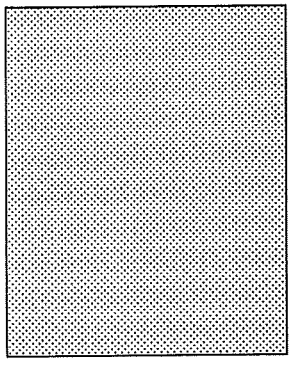
TYPE C
(RETICULAR AND LINEAR OPACITIES)
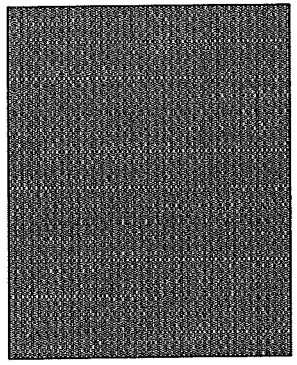
TYPE D
(NODULAR OPACITIES)
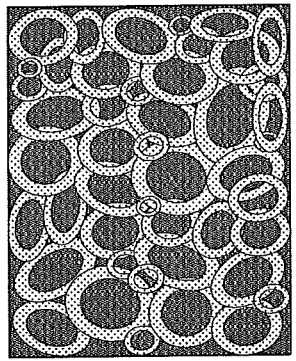
TYPE E
(HONEYCOMBING)
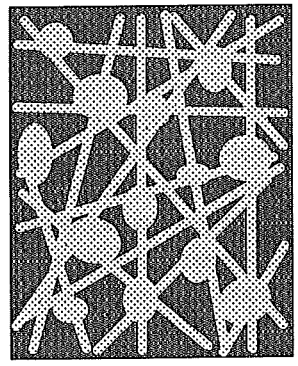
TYPE F
(CONSOLIDATION)
FIG. 6

LOOKUP TABLE FOR ESTIMATING CHANGE DIRECTION OF
DISEASE STATE [DISEASE CAUSE $\alpha$]

|  |  | SECOND IMAGE (EXAMINATION 2) | | | |
|---|---|---|---|---|---|
|  |  | TYPE A | TYPE B | TYPE C | TYPE D |
| FIRST IMAGE (EXAMINATION 1) | TYPE A | NO CHANGE (0) | EXACERBATION (+) | EXACERBATION (+) | EXACERBATION (+) |
|  | TYPE B | RECOVERY (−) | NO CHANGE (0) | EXACERBATION (+) | EXACERBATION (+) |
|  | TYPE C | RECOVERY (−) | RECOVERY (−) | NO CHANGE (0) | EXACERBATION (+) |
|  | TYPE D | RECOVERY (−) | RECOVERY (−) | RECOVERY (−) | NO CHANGE (0) |

DISEASE STATE IS CHANGED FROM TYPES OF TEXTURE PATTERNS
IN EXAMINATION 1 TO TYPES OF TEXTURE PATTERNS IN EXAMINATION 2

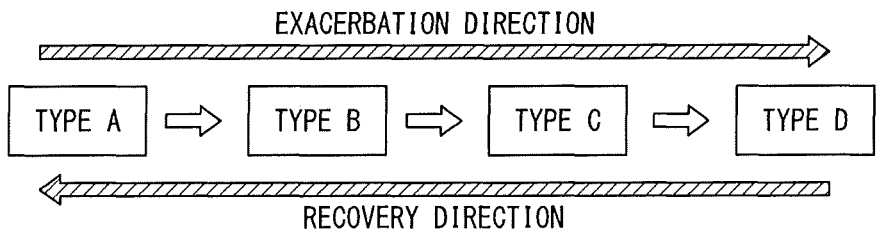

FIG. 8

LOOKUP TABLE FOR ESTIMATING CHANGE DIRECTION OF
DISEASE STATE AND RATE OF CHANGE [DISEASE CAUSE α]

|  | SECOND IMAGE (EXAMINATION 2) | | | |
|---|---|---|---|---|
| FIRST IMAGE (EXAMINATION 1) | TYPE A | TYPE B | TYPE C | TYPE D |
| TYPE A | NO CHANGE (0) | EXACERBATION (+1) | EXACERBATION (+2) | EXACERBATION (+3) |
| TYPE B | RECOVERY (−1) | NO CHANGE (0) | EXACERBATION (+1) | EXACERBATION (+2) |
| TYPE C | RECOVERY (−2) | RECOVERY (−1) | NO CHANGE (0) | EXACERBATION (+1) |
| TYPE D | RECOVERY (−3) | RECOVERY (−2) | RECOVERY (−1) | NO CHANGE (0) |

DISEASE STATE IS CHANGED FROM TYPES OF TEXTURE PATTERNS
IN EXAMINATION 1 TO TYPES OF TEXTURE PATTERNS IN EXAMINATION 2

(0) : NO CHANGE
(+1) : EXACERBATION (SLOW EXACERBATION RATE)
(+2) : EXACERBATION (MEDIUM EXACERBATION RATE)
(+3) : EXACERBATION (RAPID EXACERBATION RATE)
(−1) : RECOVERY (SLOW RECOVERY RATE)
(−2) : RECOVERY (MEDIUM RECOVERY RATE)
(−3) : RECOVERY (RAPID RECOVERY RATE)

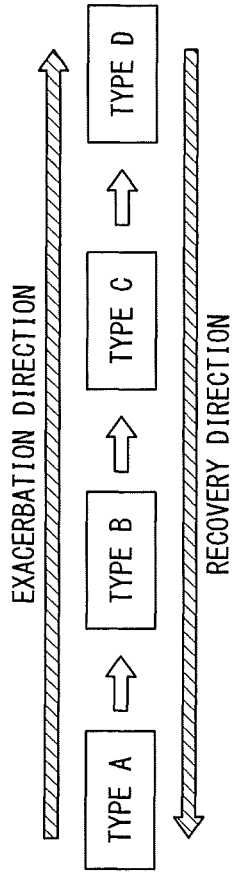

TYPE A → TYPE B → TYPE C → TYPE D

EXACERBATION DIRECTION
RECOVERY DIRECTION

FIG. 11

LOOKUP TABLE FOR ESTIMATING CHANGE DIRECTION OF DISEASE STATE [DISEASE CAUSE α]

| FIRST IMAGE (EXAMINATION 1) \ SECOND IMAGE (EXAMINATION 2) | TYPE A | TYPE B | TYPE C | TYPE D |
|---|---|---|---|---|
| TYPE A | NO CHANGE (0) | EXACERBATION (+) | EXACERBATION (+) | EXACERBATION (+) |
| TYPE B | RECOVERY (−) | NO CHANGE (0) | EXACERBATION (+) | EXACERBATION (+) |
| TYPE C | RECOVERY (−) | RECOVERY (−) | NO CHANGE (0) | EXACERBATION (+) |
| TYPE D | RECOVERY (−) | RECOVERY (−) | RECOVERY (−) | NO CHANGE (0) |

LOOKUP TABLE FOR ESTIMATING CHANGE DIRECTION OF DISEASE STATE [DISEASE CAUSE γ]

| FIRST IMAGE (EXAMINATION 1) \ SECOND IMAGE (EXAMINATION 2) | TYPE A | TYPE B | TYPE H | TYPE J |
|---|---|---|---|---|
| TYPE A | NO CHANGE (0) | EXACERBATION (+) | EXACERBATION (+) | EXACERBATION (+) |
| TYPE B | RECOVERY (−) | NO CHANGE (0) | EXACERBATION (+) | EXACERBATION (+) |
| TYPE H | RECOVERY (−) | RECOVERY (−) | NO CHANGE (0) | EXACERBATION (+) |
| TYPE J | RECOVERY (−) | RECOVERY (−) | RECOVERY (−) | NO CHANGE (0) |

LOOKUP TABLE FOR ESTIMATING CHANGE DIRECTION OF DISEASE STATE [DISEASE CAUSE β]

| FIRST IMAGE (EXAMINATION 1) \ SECOND IMAGE (EXAMINATION 2) | TYPE A | TYPE B | TYPE E | TYPE F |
|---|---|---|---|---|
| TYPE A | NO CHANGE (0) | EXACERBATION (+) | EXACERBATION (+) | EXACERBATION (+) |
| TYPE B | RECOVERY (−) | NO CHANGE (0) | EXACERBATION (+) | EXACERBATION (+) |
| TYPE E | RECOVERY (−) | RECOVERY (−) | NO CHANGE (0) | EXACERBATION (+) |
| TYPE F | RECOVERY (−) | RECOVERY (−) | RECOVERY (−) | NO CHANGE (0) |

LOOKUP TABLE FOR ESTIMATING CHANGE DIRECTION OF DISEASE STATE [DISEASE CAUSE δ]

| FIRST IMAGE (EXAMINATION 1) \ SECOND IMAGE (EXAMINATION 2) | TYPE A | TYPE B | TYPE K | TYPE F |
|---|---|---|---|---|
| TYPE A | NO CHANGE (0) | EXACERBATION (+) | EXACERBATION (+) | EXACERBATION (+) |
| TYPE B | RECOVERY (−) | NO CHANGE (0) | EXACERBATION (+) | EXACERBATION (+) |
| TYPE K | RECOVERY (−) | RECOVERY (−) | NO CHANGE (0) | EXACERBATION (+) |
| TYPE F | RECOVERY (−) | RECOVERY (−) | RECOVERY (−) | NO CHANGE (0) |

FIG. 14

MEDICAL IMAGE PROCESSING APPARATUS, MEDICAL IMAGE PROCESSING SYSTEM, AND MEDICAL IMAGE PROCESSING METHOD

CROSS-REFERENCE TO RELATED APPLICATIONS

This application is based upon and claims the benefit of priority from Japanese Patent Application No. 2018-154776, filed on Aug. 21, 2018 and Japanese Patent Application No. 2019-126353 filed on Jul. 5, 2019, the entire contents of each of which are incorporated herein by reference.

FIELD

Embodiments described herein relate generally to a medical image processing apparatus, a medical image processing system, and a medical image processing method.

BACKGROUND

Nowadays, various diseases are diagnosed by analyzing image data generated by imaging an object with a modality such as an X-ray computed tomography (CT) apparatus, a magnetic resonance imaging (MRI) apparatus, and an ultrasonic diagnostic apparatus.

For example, diagnosis of diffuse pulmonary disease is performed by using X-ray images and/or X-ray CT images. The diffuse pulmonary disease is a generic term for lung diseases in which the lesions are spread relatively evenly to the right and left lungs, and the diffuse pulmonary disease includes various diseases. Interstitial pneumonia is a representative case of the diffuse pulmonary disease, and there are also diffuse pulmonary diseases attributable to infections and tumors. The interstitial pneumonia is not a single disease. In a broad sense, the interstitial pneumonia includes collagen disease, hypersensitivity pneumonia, pneumoconiosis, and occupational lung disease, besides idiopathic interstitial pneumonia that is the most frequent case. Thus, the diffuse pulmonary disease can be classified into many individual disease types, which may be referred to as disease causes in the following description.

X-ray CT images of the diffuse pulmonary disease are known to be classified into several types of texture patterns. In a proposed method, texture analysis is performed on a pulmonary X-ray CT image to classify the lung field into several texture patterns, and the volume ratio of each texture pattern to the entire lung field and its temporal change are displayed.

However, these conventional techniques cannot grasp the change in disease state in the local region of the tissue such as the lung. For example, these conventional techniques cannot grasp whether the local region is in the recovery direction or in the exacerbation direction.

BRIEF DESCRIPTION OF THE DRAWINGS

In the accompanying drawings:

FIG. 4 is a schematic diagram illustrating the first image and the second image.

FIG. 6 is a schematic diagram illustrating different types of texture patterns;

FIG. 8 is a schematic diagram illustrating a lookup table for estimating a change direction of a disease state;

FIG. 11 a schematic diagram illustrating a lookup table for estimating the change direction of the disease state and the rate of change;

FIG. 14 is a schematic diagram illustrating lookup tables for estimating the change direction of the disease state for each disease cause;

DETAILED DESCRIPTION

A description will now be given of embodiments of medical image processing apparatuses, medical image processing systems, and medical image processing methods by referring to the accompanying drawings. In the following embodiments, components assigned with the same reference sign are assumed to function and operate in the same manner, and duplicate description is omitted.

In one embodiment, a medical image processing apparatus includes a memory storing a predetermined program and processing circuitry. The processing circuitry is configured, by executing the predetermined program, to acquire a plurality of images that are obtained by imaging a same object and are different in imaging time, classify tissue property of the object into a plurality of tissue-property classes by analyzing the tissue property of the object based on pixel values of respective regions of the plurality of images, assign the classified tissue-property classes to the respective regions of the plurality of images, and estimate change in disease state of the object from the change in the classified tissue-property classes in the respectively corresponding regions of the plurality of images.

Figure 1:
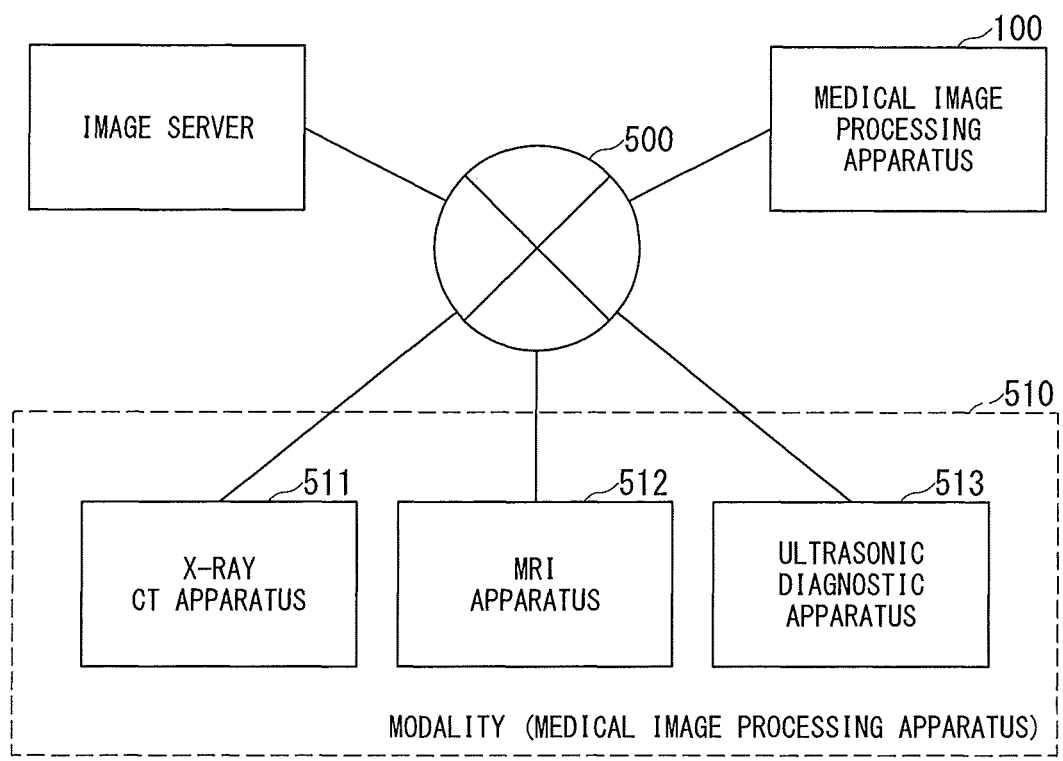
FIG. 1 is a configuration diagram illustrating a medical image diagnostic system that includes the medical image processing apparatus according to the first embodiment.

FIG. 1 is a configuration diagram illustrating a medical image processing system that includes the medical image processing apparatus 100 according to embodiments. The medical image processing system is, for example, a processing system configured to perform a series of processing steps related to medical images in a hospital, such as acquiring medical images, performing image processing on the medical images, storing the medical images, and using the medical images for diagnosis.

The medical image processing system includes an image server, the medical image processing apparatus 100, and at least one modality 510 (i.e., medical image diagnostic apparatus 510) for acquiring medical images from an object such as a patient, as exemplified by an X-ray CT apparatus 511, an MRI apparatus 512, and an ultrasonic diagnostic apparatus 513. The image server, the medical image processing apparatus 100, and the modality 510 are interconnected via, for example, a network 500 in the hospital so that various data and medical images can be exchanged.

Configuration of First Embodiment

Figure 2:
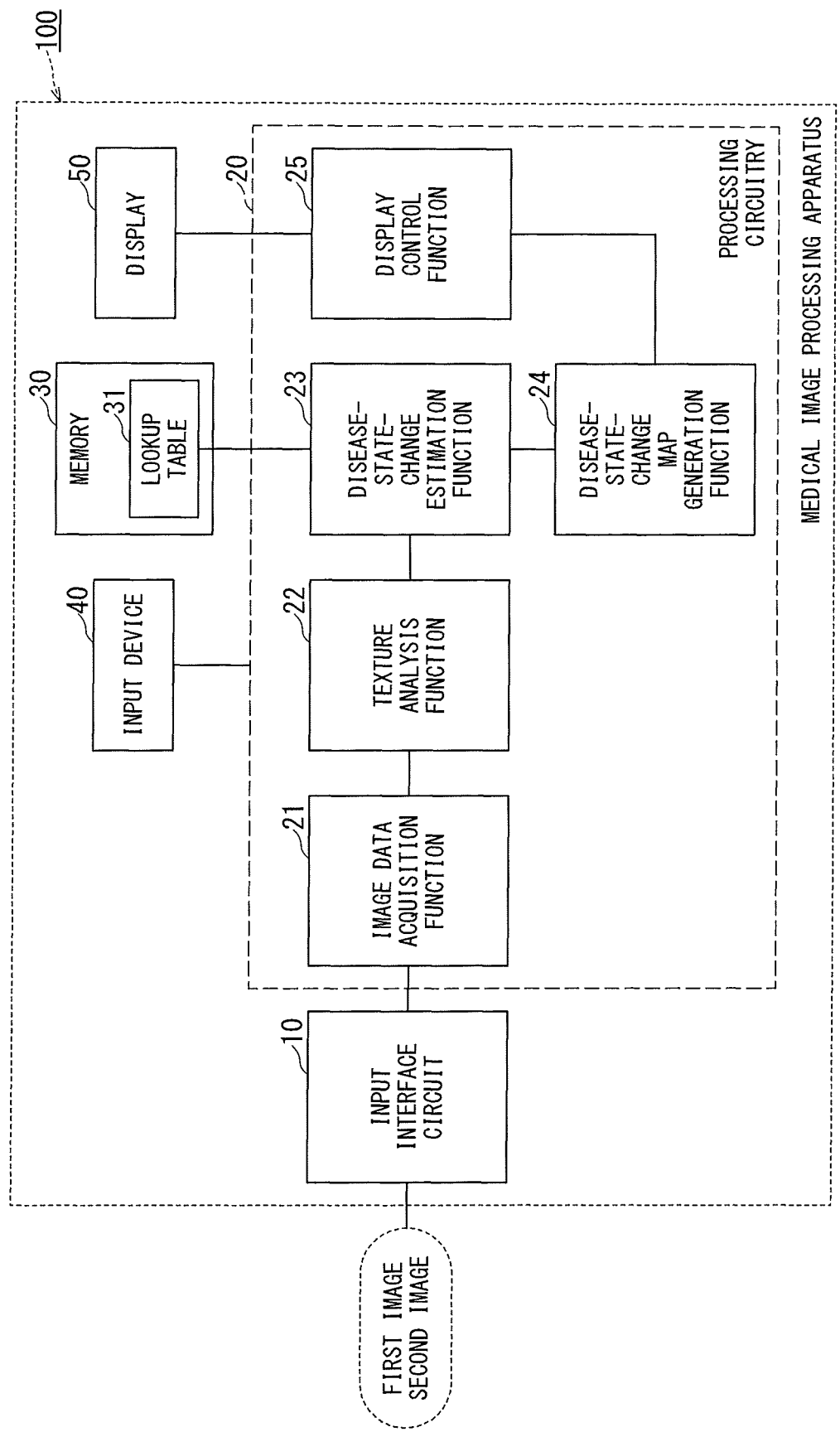
FIG. 2 is a block diagram illustrating the configuration of the medical image processing apparatus according to the first embodiment.

FIG. 2 is a block diagram illustrating the configuration of the medical image processing apparatus 100 according to the first embodiment. The medical image processing apparatus 100 includes, for example, an input interface circuit 10, processing circuitry 20, a memory 30, an input device 40, and a display 50. The medical image processing apparatus 100 is configured as, for example, a so-called work station or a high-performance personal computer.

The input interface circuit 10 is an interface circuit for inputting data via a storage medium such as an optical disk and/or a USB memory and for inputting data via a wired or wireless network or a special-purpose or general-purpose communication line. The medical image processing apparatus 100 of the first embodiment acquires the first and second images imaged by the modality 510 such as the X-ray CT apparatus 511 or the first and second images stored in the image server, via the input interface circuit 10.

Note that the first image and the second image are images obtained by imaging the same subject at different dates and times. For example, the second image is an image imaged at a date and time later than the imaging date of the first image. The first image and the second image will be described below in more detail.

The memory 30 is a recording medium including a read-only memory (ROM) and a random access memory (RAM) in addition to an external memory device such as a hard disk drive (HDD) and/or an optical disc device. The memory 30 stores various programs executed by a processor of the processing circuitry 20 as well as various types of information and data including a lookup table 31 described below.

The input device 40 includes various devices for an operator to input various types of information and data, and is configured of a mouse, a keyboard, a trackball, and a touch panel, for example.

The display 50 is a display device such as a liquid crystal display panel, a plasma display panel, and an organic EL panel.

The processing circuitry 20 is a circuit that includes a central processing unit (CPU) and/or a special-purpose or general-purpose processor, for example. The processor implements various functions described below by executing the programs stored in the memory 30. The processing circuitry 20 may be configured of hardware such as an FPGA and an ASIC. The various functions described below can also be implemented by such hardware. Additionally, the processing circuitry 20 can implement the various functions by combining hardware processing and software processing based on its processor and programs.

Further, the processing circuitry 20 may be configured by combining a plurality of independent processors such that the processors implement the respective functions. When the processing circuitry 20 is provided with the plurality of processors, a memory for storing the programs may be provided for each processor or one memory may collectively store all the programs corresponding to all the processors.

Operation of First Embodiment

The processing circuitry 20 of the first embodiment implements the respective functions shown in FIG. 2, i.e., an image data acquisition function 21, a texture analysis function 22, a disease-state-change estimation function 23, a disease-state-change map generation function 24, and a display control function 25. The processing circuitry 20 implements each of these functions by causing a processer included in the processing circuitry 20 to execute a predetermined program stored in the memory 30.

The image data acquisition function 21 acquires images that are obtained by imaging the same object and different in imaging time. For example, the image data acquisition function 21 acquires the first image imaged at the first date and time and the second image imaged at the second date and time that is after the first date and time. The first image and the second image may be, for example, X-ray images and/or X-ray CT images obtained by imaging the lung, although not limited to these images.

The texture analysis function 22 classifies respective regions of the images acquired by the image data acquisition function 21 into different texture patterns. For example, the texture analysis function 22 performs known texture analysis on the first and second images acquired by the image data acquisition function 21 so as to classify the respective regions of the first image and the second image into different texture patterns.

The disease-state-change estimation function 23 estimates change in disease state of the object, based on change in texture pattern between corresponding regions in the respective images classified by the texture analysis function 22. For example, the disease-state-change estimation function 23 estimates whether the change direction of the object's disease state in the local region is (a) recovery, (b) exacerbation, or (c) no change, on the basis of the change in texture pattern in the corresponding local regions in the first and second images. For example, the above-described "corresponding local regions" or "corresponding regions" mean respective regions that depict anatomically the same portion (i.e., the same organ, or the same tissue) of the same object, among plural images.

The disease-state-change map generation function 24 generates a disease-state-change map in which the change direction of the disease state estimated by the disease-state-change estimation function 23 is depicted for every one pixel or for every one pixel group consisting of two or more pixels. For example, the disease-state-change map generation function 24 generates the disease-state-change map such that the change direction of the disease state is distinguishably depicted for every one pixel or for every one pixel group, with different manners, including at least one of different chromatic colors, different grayscale, different numbers, and different signs.

The display control function 25 causes the display 50 to display the generated disease-state-change map, for example, in response to a user's instruction.

Figure 3:
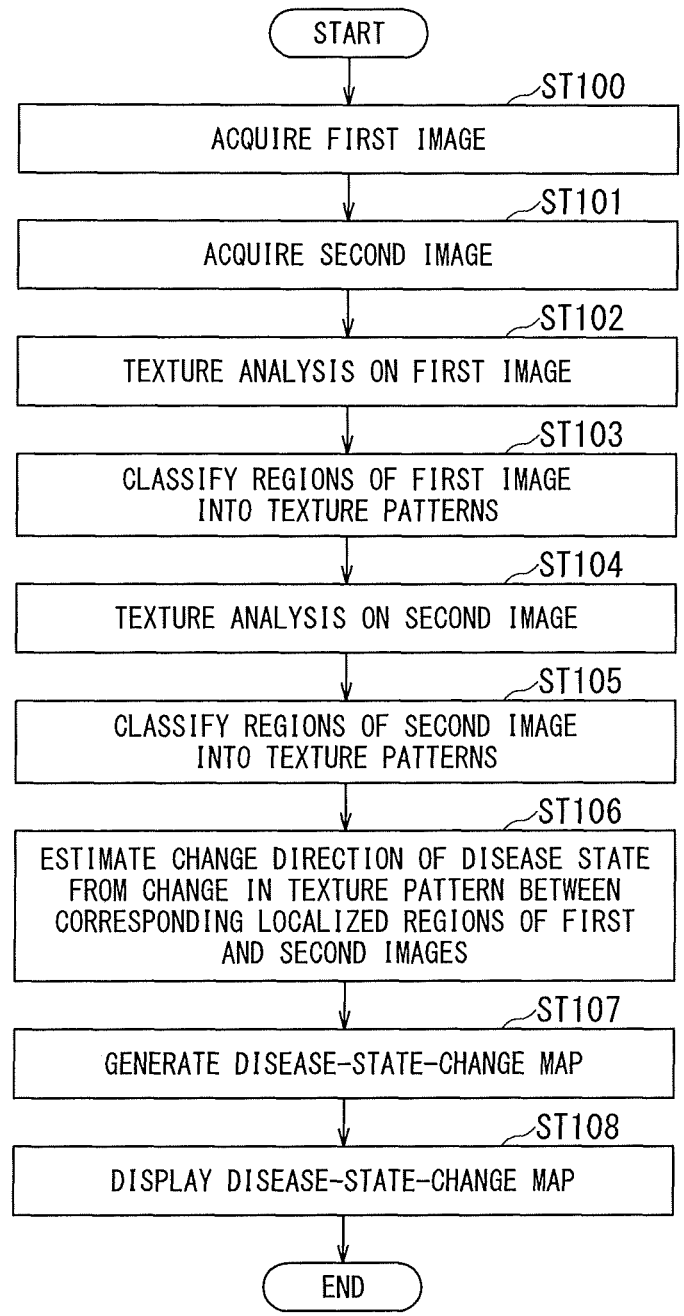
FIG. 3 is a flowchart illustrating processing performed by the medical image processing apparatus according to the first embodiment.

FIG. 3 is a flowchart illustrating processing performed by the medical image processing apparatus 100 according to the first embodiment. FIG. 4 to FIG. 9 are schematic diagrams for illustrating the operation concept of the medical image processing apparatus 100 according to the first embodiment. Details of the operation of the medical image processing apparatus 100 will now be described on the basis of the step number of FIG. 3 by referring to FIG. 4 to FIG. 9 as required.

First, the first image is acquired in the step ST100 of FIG. 3, and the second image is acquired in the step ST101. FIG. 4 is a schematic diagram illustrating the first image and the second image. The first image and the second image are images that are obtained by imaging the same subject and are different in imaging timing. The first image is, for example, an image imaged in Examination 1 performed on May 8, 2018. The second image is an image imaged in Examination 2 performed on a later date and time (for example, Aug. 8, 2018) than Examination 1.

Although the interval between the imaging date of the first image and the imaging date of the second image is three months in the above case, this is merely one example and the interval of imaging date between the two images is determined by a doctor, such as one week, one month, six months, and 12 months. Further, the number of times of imaging is not limited to two. For example, from three or more images having different imaging dates, two desired images may be selected. In this case, one of the selected two images with earlier imaging date is treated as the first image and the other of the selected two images is treated as the second image.

It should be noted that the first and second images shown in FIG. 4 are merely schematic diagrams for illustrating the operation of the medical image processing apparatus 100 of the present embodiment. Each of the first and second images is, for example, a two-dimensional image obtained by extracting a coronal cross-section from a three-dimensional image that is obtained by imaging a lung field of the object with the use of the X-ray CT apparatus 511.

As described above, diagnosis of the diffuse pulmonary disease is performed by using X-ray images and/or X-ray CT images, for example. The treatment for the diffuse pulmonary disease is mainly drug treatment such as administration of steroids and/or immunosuppressant. In order to determine the treatment effect, it is extremely important to monitor the temporal change of the shadow pattern of the X-ray CT image, i.e., the texture pattern.

Meanwhile, it is known that X-ray CT images of a lesion area of the diffuse pulmonary disease is classified into several types of texture patterns. It is also known that the type of texture pattern changes as the disease progresses from the initial state in the exacerbation direction. Conversely, when the therapeutic effect is improved and the disease state changes from exacerbation to recovery, it is known that the type of texture pattern also changes.

FIG. 4 schematically illustrates such temporal change in texture pattern in the first image and the second image. The dark region in the background (including the peripheral region) of the lung field of each of the first and second images indicates a normal region without a disease. In FIG. 4, in addition to the dark background region, regions indicated by light hatching are illustrated. In FIG. 4, these light hatched regions correspond to the diseased regions. Note that different hatching patterns in FIG. 4 correspond to different grayscale patterns (i.e., different texture patterns) in X-ray CT images.

In the case of FIG. 4, in the right lung (i.e., the lung depicted on the left side in the first and second images in FIG. 4) among the right and left lungs of the object, the same type of light-colored texture pattern is observed between the first image and the second image. However, it should be noted that the region of the texture pattern in the right lung of the second image is larger than the region of the texture pattern in the right lung of the first image. In other words, the diseased region in the right lung is larger at the time of Aug. 8, 2018, when the second image is acquired (three months after acquisition of the first image), than at the time of May 8, 2018 when the first image is acquired, which means that the disease is in the exacerbation direction for the right lung.

As for the left lung (the lung depicted on the right side in the first and second images in FIG. 4), though a texture pattern of a type different from that of the right lung is generated over a wide range in the first image, the diseased region corresponding to this type of texture pattern is smaller in the second image. Further, in the second image, in the lower part of the left lung, a texture pattern of a type different from the above two types is generated. This means that the region in the recovery direction and the region in the exacerbation direction are mixed in the left lung.

Conventionally, change in texture patterns in such X-ray CT images has often been left to subjective evaluation of a doctor. In view of this problem, the medical image processing apparatus 100 of the present embodiment detects local change in type of texture pattern, and uses this detected result for objectively estimating the change direction of the disease state, such as whether the disease is in the recovery direction or in the exacerbation direction.

Returning to FIG. 3, in the step ST102, the texture analysis is performed on the acquired first image. In the next step ST103, the respective regions of the first image are classified into different texture patterns on the basis of the texture analysis result. Similarly, in the step ST104, the texture analysis is performed on the acquired second image. In the next step ST105, the respective regions of the second image are classified into different texture patterns on the basis of the texture analysis result.

Figure 5:
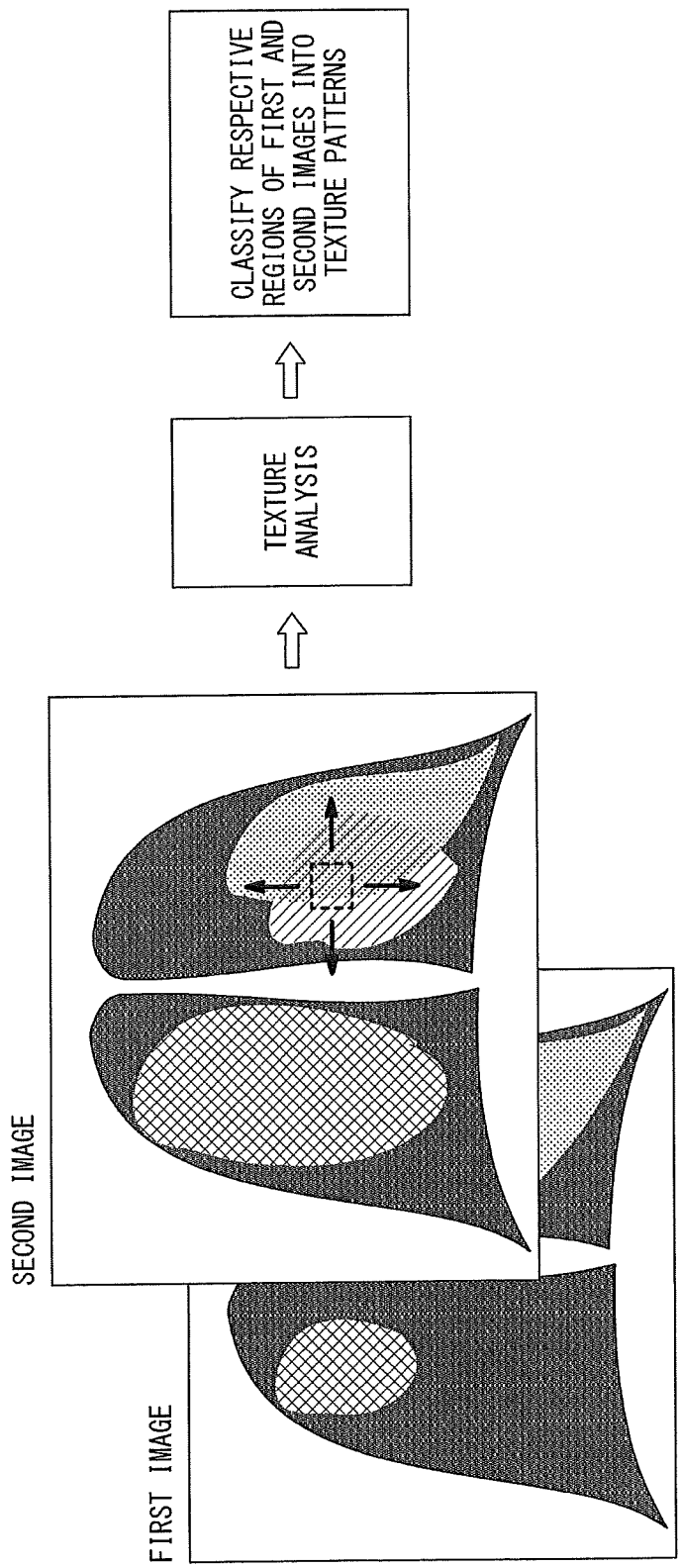
FIG. 5 is a schematic diagram illustrating the processing concept of the steps ST102 to ST105 in the flowchart of FIG. 3.

FIG. 5 is a schematic diagram illustrating the processing concept of the steps ST102 to ST105. The region surrounded by the broken-line square shown in the second image of FIG. 5 is a determination window of the texture analysis. In the texture analysis, for example, feature amount of the target region is calculated by analyzing the pixel values in the determination window (in the case where the analysis target image is an X-ray CT image, the CT value for each pixel may be used). For example, statistics such as an average value and/or a standard deviation of pixel values, histogram distribution of pixel values, or parameters related to spectrum distribution are calculated as the feature amount.

By shifting the determination window in the left, right, up, and down directions, the distribution of the feature amount of the entire image can be calculated as illustrated in FIG. 5, for example. The determination window may be shifted every one pixel or every two or more pixels. Additionally or alternatively, the entire image may be previously divided into pixel groups, each of which is the same in size as the determination window, so that the feature amount in each pixel group is calculated sequentially or in parallel.

In the step ST103, the respective regions of the first image are classified into several or many types of different texture patterns on the basis of the calculated feature amount.

Similarly, in the steps ST105, the respective regions of the second image are classified into several or many types of different texture patterns on the basis of the calculated feature amount.

For example, a medical image (such as an X-ray CT image) of a diseased region such as diffuse pulmonary disease is classified into a plurality of types of texture patterns in a manner disclosed in Non-Patent Document 1.

[Non-Patent Document 1] Uchiyama Y, Katsuragawa S, Abe H, et al. Quantitative computerized analysis of diffuse lung disease in high-resolution computed tomography. Med Phys. AAPM; 2003; 30(9):2440-2454.

For example, as shown in FIG. 6, each of the first and second images may be classified into a normal texture pattern indicated as the type "A" and five abnormal texture patterns that include the type "B", the type "C", the type "D", the type "E", and the type "F".

In detail, the above-described different texture patterns include the normal pattern indicated as the type "A", the ground-glass opacities pattern indicated as the type "B", the reticular and linear opacities pattern indicated as the type "C", the nodular opacities pattern indicated as the type "D", the honeycombing pattern indicated as the type "E", and the consolidation pattern indicated as the type "F".

Each texture pattern in FIG. 6 is shown for merely illustrating the operation of the present embodiment, and is not intended for medical correctness or accuracy.

Figure 7:
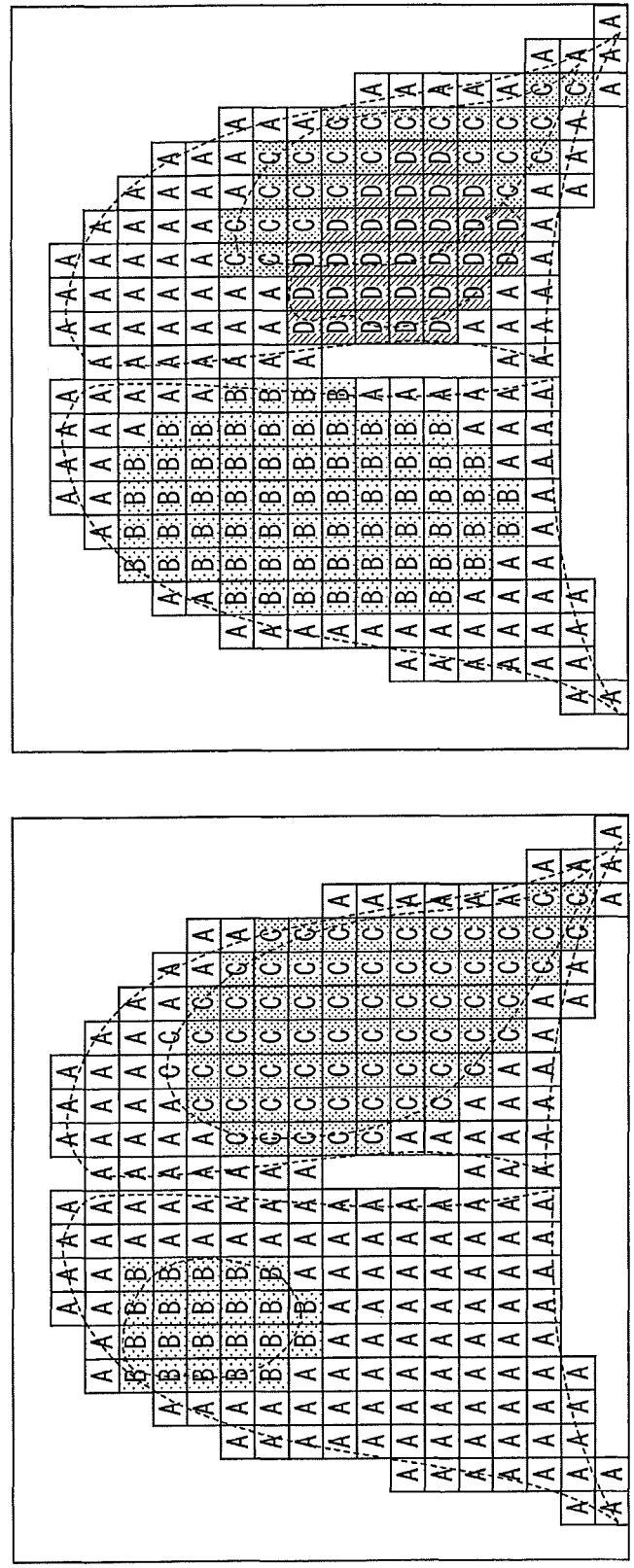
FIG. 7 is a schematic diagram illustrating a case where right and left lung regions are classified into different texture patterns.

FIG. 7 is a schematic diagram illustrating a case where right and left lung regions of each of the first and second images are classified into different texture patterns by the processing in the steps ST103 and ST105.

In the first image shown in FIG. 7, the upper part of the right lung is classified into the type "B" indicative of the ground-glass opacities pattern, the remaining regions of the right lung is classified into the type "A" indicative of the normal pattern, while a large part of the left lung is classified into the type "C" indicative of the reticular and linear opacities pattern.

In the second image shown in FIG. 7, most of the right lung is classified into the type "B" indicative of the ground-glass opacities pattern, while the left lung is classified into the type "C" indicative of the reticular and linear opacities pattern and the type "D" indicative of nodular opacities pattern except the peripheral regions classified into the type "A" indicative of the normal pattern.

In the case of FIG. 7, the respective regions of the right and left lungs are classified into different texture patterns by a square mesh that consists of many pixel groups of the same size (for example, 5×5 pixel groups), resulting in the resolution of 5×5 pixel groups.

However, as described above, the distribution of the feature amount can be calculated for each pixel by shifting the determination window of a predetermined size in the horizontal and vertical directions for every one pixel. In this case, distribution of different texture patterns can be determined so smoothly that the distribution changes for each pixel, resulting in that the resolution of a single pixel can be obtained.

Returning to FIG. 3, in the step ST106, after performing registration between the first and the second images as necessary, the change direction in the disease state is estimated from change in texture pattern between each local region of the first image and the corresponding local region of the second image.

The above-described estimation of the change direction in the disease state means to estimate whether the direction of the disease state, i.e., the state of the diseased region is (a) recovery, (b) exacerbation, or (c) no change. The change direction of the disease state can be estimated, for example, by referring to the lookup table 31 in which the transition of the texture patterns is associated with the change direction of the disease state (i.e., whether the diseased region is in recovery, in exacerbation, or not changing). The lookup table 31 is stored, for example, in the memory 30. The disease-state-change estimation function 23 of the processing circuitry 20 reads the lookup table 31 from the memory 30 and uses it for the processing of the step ST106.

The upper part of FIG. 8 illustrates the lookup table 31 for estimating the change direction of the disease state. The lower part of FIG. 8 shows the change direction of the disease state and the transition of the texture patterns.

The lower part of FIG. 8 indicates the following two points. Firstly, as the texture pattern in the diseased region transitions from the type "A" to type "B", further to the type "C", and further to the type "D", the disease state changes in the exacerbation direction from the normal state toward the exacerbated state. Secondly, as the texture pattern in the diseased region transitions from the type "D" to the type "C", further to the type "B", and further to the type "A", the disease state changes in the recovery direction from the exacerbated state toward the normal state.

The relationship between the change direction of the disease state and the transition of the texture patterns shown in the lower part of FIG. 8 can be acquired from a database that includes a large number of medical images, diagnosis results of diseases by doctors based on those medical images, and progress information of those disease cases, the database being constructed with data which have been accumulated for a long time.

The lookup table in the upper part of FIG. 8 can be acquired from the relationship between the change direction of the disease state and the transition of the texture patterns shown in the lower part of FIG. 8.

For example, in the lookup table shown in FIG. 8, the texture patterns (such as types "A", "B", "C", and "D") of the first image of a certain object imaged in Examination 1 are associated with the texture patterns of the second image of the same object imaged in Examination 2 after Examination 1 on the basis of the three indicators indicative of change in disease state (i.e., respective three indicators indicative of "no change", "exacerbation", and "recovery").

The disease-state-change estimation function 23 uses the lookup table 31 for determining the change in texture pattern between each local region of the first image and the corresponding local region of the second image. This determination result enables the disease-state-change estimation function 23 to estimate whether the change direction of the disease state of the local region of the object is recovery, exacerbation, or no change. For example, when the texture pattern of a local region classified into the type "C" in the first image changes to the type "A" or "B" in the second image, this local region is estimated to be in the recovery direction. Conversely, when the texture pattern of this local region classified into the type "C" in the first image changes to the type "D" in the second image, this local region is estimated to be in the exacerbation direction.

Note that, as described above, the diffuse pulmonary disease is known to have many disease causes. Thus, there is a possibility that the relationship between the transition of the texture patterns and the change direction of the disease state may be different, depending on the disease cause. Accordingly, the lookup table shown in FIG. 8 is associated with supplementary information in order to indicate that this lookup table corresponds to the diffuse pulmonary disease due to a specific disease cause (for example, idiopathic interstitial pneumonia). In the case of FIG. 8, a specific disease cause of "disease cause α" is attached to the upper portion of the lookup table, as the supplementary information.

In the lookup table of FIG. 8, three signs "0", "+" and "−" are described along with the three indicators "no change", "exacerbation", and "recovery", respectively. These three signs "0", "+" and "−" are for readily understanding the correspondence with the disease-state-change map illustrated in FIG. 9, and it is not necessarily required to include the information of these three signs in the lookup table.

Returning to FIG. 3, in the step ST107, the disease-state-change map generation function 24 generates the disease-state-change map in which change in disease state in each local region is depicted.

Figure 9:
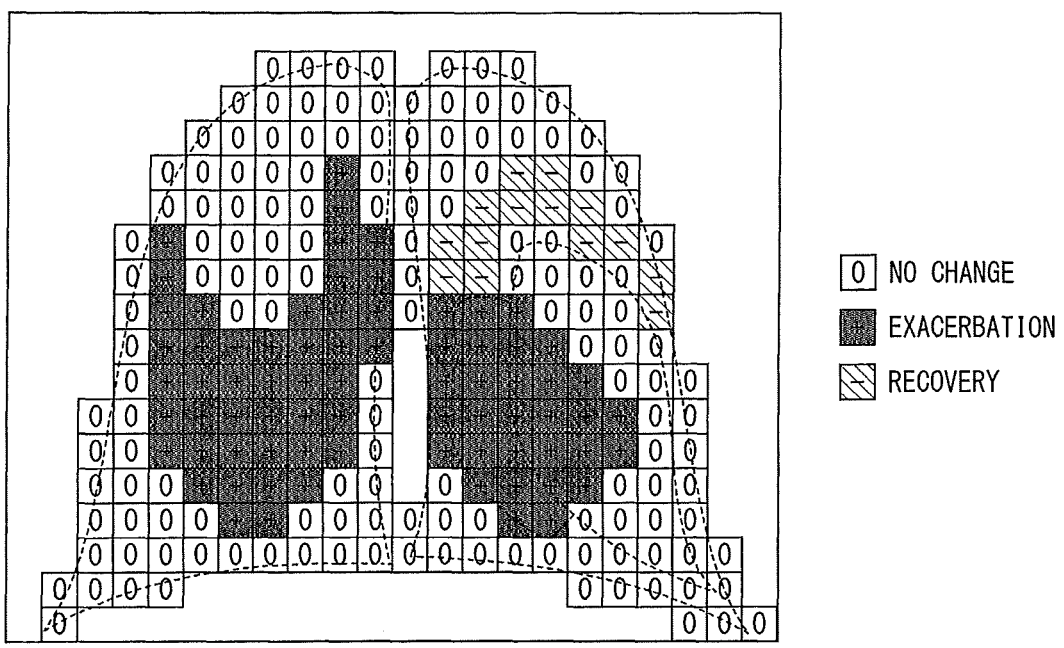
FIG. 9 is a schematic diagram illustrating a disease-state change map.

FIG. 9 is a schematic diagram illustrating the disease-state-change map. The disease-state-change map shown in FIG. 9 is generated on the basis of the lookup table shown in FIG. 8 and the first and second images shown in FIG. 7 (i.e., the two images after being classified into the texture patterns such as the type "A", type "B", type "C", and type "D".)

In FIG. 9, the local region depicted by the sign "+" indicates a local region that is estimated to have been exacerbated in the period from the imaging date of Examination 1 to the imaging date of Examination 2. The local region depicted by the sign "−" indicates a local region that is estimated to have recovered in the period from the imaging date of Examination 1 to the imaging date of Examination 2. The local region depicted by the sign "0" indicates a local region that is estimated to maintain the disease state without change in the period from the imaging date of Examination 1 to the imaging date of Examination 2.

The disease-state-change map may be depicted with such a fine resolution that a different color is assigned for every one pixel or for every one pixel group consisting of two or more pixels, similarly to the first and second images after being classified into texture patterns as shown in FIG. 7.

Although the change direction of the disease state is distinguished by using different signs such as "0", "+", and "−" in the disease-state-change map illustrated in FIG. 9, the distinguishment method is not limited to this method. For example, the disease-state-change map can be generated by using at least one of the aspects including different chromatic colors, different grayscale, different numbers, and different signs for distinguishably depicting the change direction of the disease state.

In the step ST108, the generated disease-state-change map appears on the display 50 of the medical image processing apparatus 100. Additionally or alternatively, the generated disease-state-change map may be transmitted to the modality 510 such as the X-ray CT apparatus 511 via the network 500 and be displayed on the display of the modality 510.

As described above, the medical image processing apparatus 100 of the first embodiment can readily detect the change in disease state in each local region of the tissue such as the lung, i.e., can readily detect whether each local region is in the recovery direction or in the exacerbation direction.

Modification of First Embodiment

Figure 10:
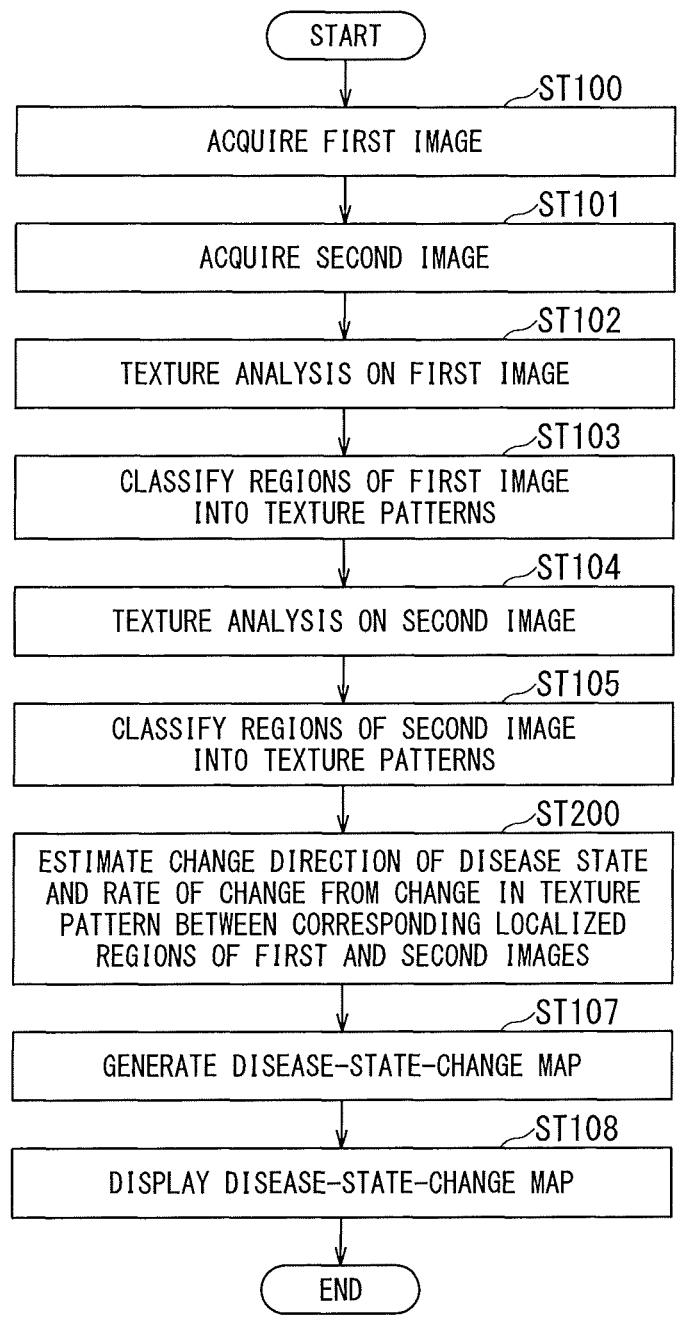
FIG. 10 is a flowchart illustrating processing performed by a medical image processing apparatus according to a modification of the first embodiment.

FIG. 10 is a flowchart illustrating processing performed by the medical image processing apparatus 100 according to a modification of the first embodiment. The processing in the modification differs from the first embodiment only in the step ST200, and the other processing is the same as that of the first embodiment.

In the step ST200, not only the change direction of the disease state but also the rate of change in disease state are further estimated from the change in texture pattern between each local region of the first image and the corresponding local region of the second image. In detail, the disease-state-change estimation function 23 estimates the rate of exacerbation, such as whether the disease of the relevant tissue is being gradually exacerbated or being rapidly exacerbated. Similarly, the disease-state-change estimation function 23 estimates the rate of recovery, such as whether the disease of the relevant tissue is gradually recovering or is rapidly recovering.

In the modification of the first embodiment, in order to estimate the rate of change in disease state, the disease-state-change estimation function 23 uses a lookup table (FIG. 11) in which information on the rate of change is added to the lookup table (FIG. 8) for estimating the change direction of disease state.

In the lookup table shown in FIG. 11, for example, if a local region of the first image in Examination 1 is classified into the type "A" of the texture pattern and the same local region in the second image is also classified into the type "A", this local region is determined as "no change". If this local region (classified into the type "A." in the first image) is classified into the type "B" in the second image, the change direction of the disease state is determined as the exacerbation direction with slow rate. If this local region (classified into the type "A" in the first image) is classified into the type "C" in the second image, the change direction of the disease state is determined as the exacerbation direction with medium rate. If this local region (classified into the type "A" in the first image) is classified into the type "D" in the second image, the change direction of the disease state is determined as the exacerbation direction with rapid rate.

On the other hand, for example, if the local region of the first image in Examination 1 is classified into the type "D" of the texture pattern and the same local region in the second image is also classified into the type "D", this local region is determined as "no change". If this local region (classified into the type "D" in the first image) is classified into the type "C" in the second image, the change direction of the disease state is determined as the recovery direction with slow rate. If this local region (classified into the type "D" in the first image) is classified into the type "B" in the second image, the change direction of the disease state is determined as the recovery direction with medium rate. If this local region (classified into the type "D" in the first image) is classified into the type "A" in the second image, the change direction of the disease state is determined as the recovery direction with rapid rate.

Thus, the rate of change in disease state in the lookup table in FIG. 11 is determined on the basis of transition distance between the type of texture pattern for a certain region in the first image and the type of texture pattern for the corresponding region in the second image as shown in the lower part of FIG. 11.

In the lookup table shown in FIG. 11, the rate in the exacerbation direction is represented by the positive number of "+1", "+2", and "+3" such that smaller number corresponds to slower rate. Similarly, the rate in the recovery direction is represented by the negative number of "−1", "−2", and "−3" such that smaller absolute value of the negative number corresponds to slower rate.

By replacing the signs "+", "−", and "0" in the disease-state-change map shown in FIG. 9 with sign number such as "+1", "+2", "+3", "−1", "−2", and "−3", the disease-state-change map generation function 24 can generate a disease-state-change map in which the rate of change in disease state is also depicted in addition to the change direction of the disease state.

Figure 12:
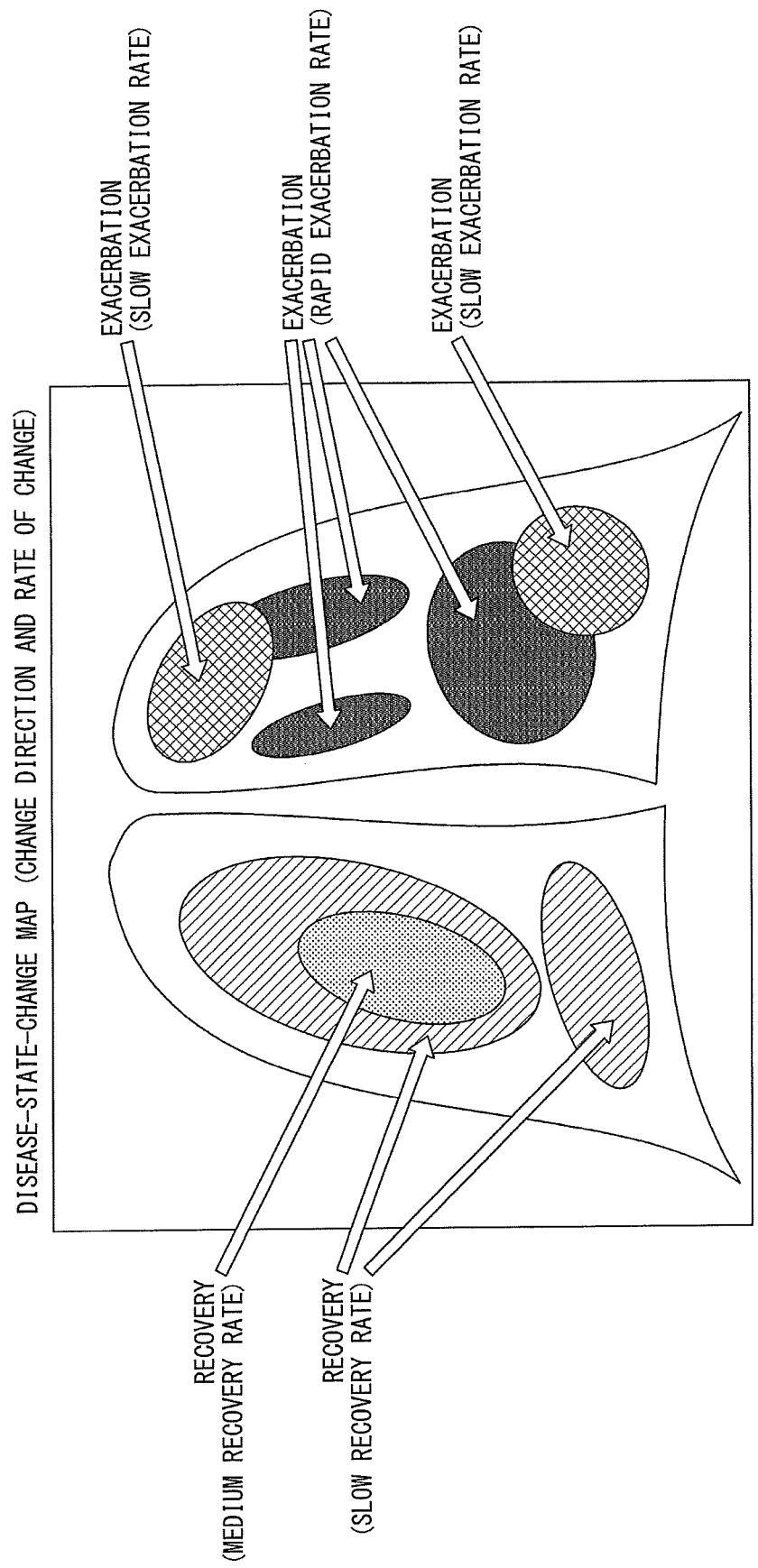
FIG. 12 is a schematic diagram illustrating a disease-state change map in which the change direction and the rate of change in disease state are depicted.

FIG. 12 is a schematic diagram illustrating a disease-state-change map in which the change direction and rate of change in disease state are depicted by using distinguishment information other than signs and number. In the disease-state-change map shown in FIG. 12, the change direction and rate of change in disease state are depicted by the type of hatching pattern and the shading (i.e., grayscale) of the hatching.

In the modification of the first embodiment, the disease-state-change map is generated so as to include or depict information on exacerbation rate and recovery rate in addition to the change direction of the disease state such as "exacerbation", "recovery", and "no change", and thus objective and accurate diagnosis can be achieved.

The rate of change in disease state such as exacerbation rate and recovery rate is, as mentioned above, determined on the basis of the transition distance between types of texture pattern in the above case. However, the rate of change in disease state may be estimated on the basis of length of the period between the imaging date of the first image in Examination 1 and the imaging date of the second image in Examination 2. Alternatively or additionally, the rate of change in disease state may be estimated on the basis of both of the transition distance between the types of texture pattern and the length of the period between the imaging date of the first image in Examination 1 and the imaging date of the second image in Examination 2.

For example, when the interval between the imaging date of the first image and the imaging date of the second image is three months and the type "A" of the texture pattern in the first image of Examination 1 transitions to the type "B" in the second image, the change direction of the disease state is determined as the exacerbation direction with slow rate. In the above-described case, when the interval between the imaging dates of the first and second images is one month and the remaining conditions are the same, the exacerbation rate is determined not as slow rate but as medium or rapid rate.

Second Embodiment

Figure 13:
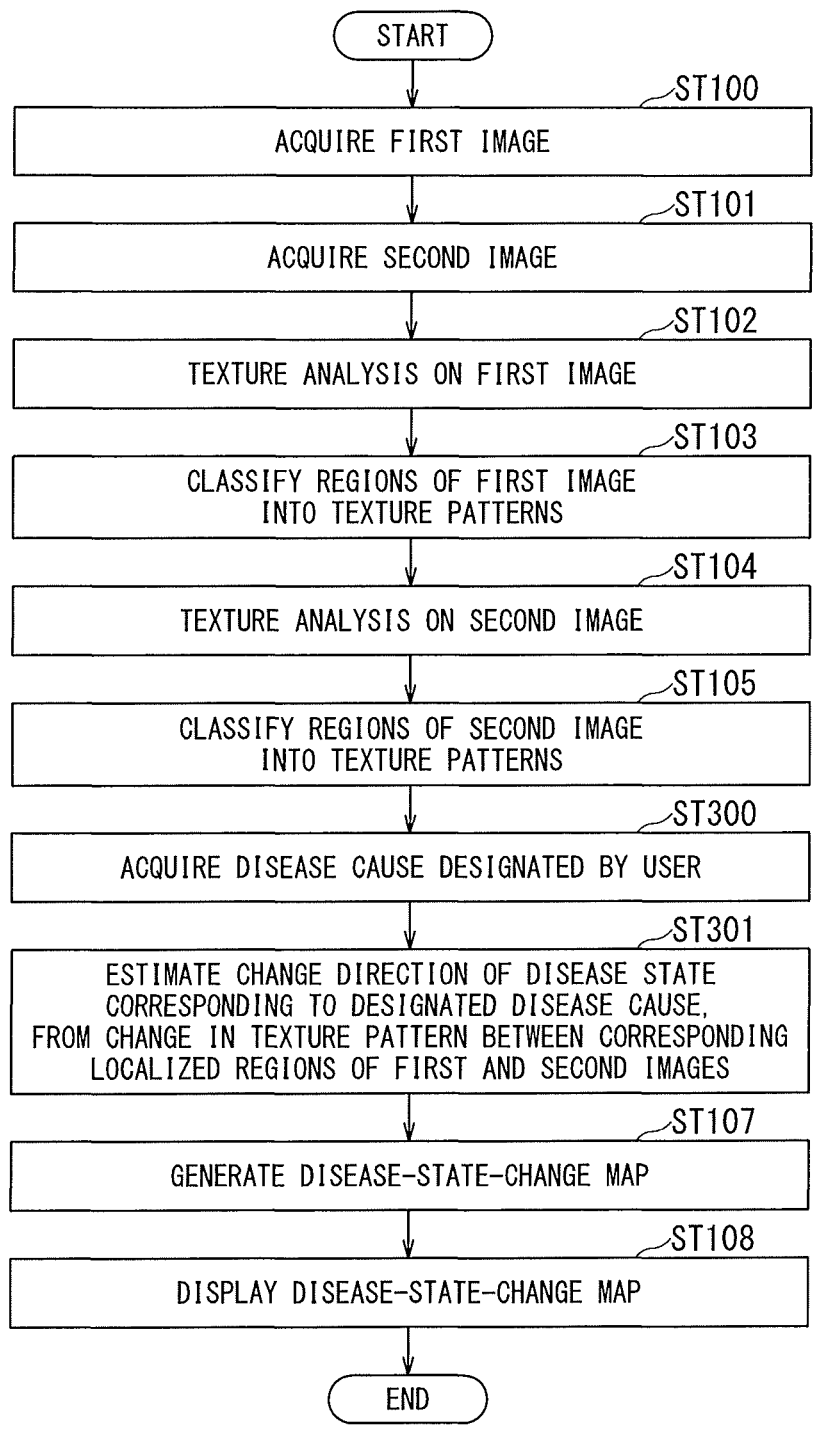
FIG. 13 is a flowchart illustrating processing performed by the medical image processing apparatus according to the second embodiment.

FIG. 13 is a flowchart illustrating processing performed by the medical image processing apparatus 100 according to the second embodiment. As described above, the diffuse pulmonary disease is known to have many disease causes, and the relationship between types of texture pattern and the change direction of the disease state may be different for each disease cause. Thus, the medical image processing apparatus 100 according to the second embodiment stores respective lookup tables that correspond to individual disease causes and are used for estimating the change direction of the disease state for each disease cause.

The second embodiment differs from the first embodiment in processing of the steps ST300 and ST301 in FIG. 13.

In the step ST300, the cause of the disease designated by the user such as a doctor is acquired. For example, a user uses the input device 40 such as a mouse and/or a keyboard for designating a disease cause of the diffuse pulmonary disease, such as a disease cause (α) (for example, idiopathic interstitial pneumonia), a disease cause (β) (for example, collagen), a disease cause (γ) (for example, hypersensitivity pneumonia), and a disease cause (δ) (for example, pneumoconiosis, occupational lung disease). The disease-state-change estimation function 23 of the processing circuitry 20 acquires the disease cause designated by the user.

In the next step ST301, the disease-state-change estimation function 23 estimates the change direction of the disease state on the basis of the change in type of the texture pattern between each local region in the first image and the corresponding local region in the second image and the lookup table. Here, the lookup table, which is used for estimating the change direction of the disease state, corresponds to the designated disease cause.

FIG. 14 illustrates four lookup tables that correspond to the respective four disease causes and are for estimating the change direction in the disease state.

As can be seen from the lookup table corresponding to the disease cause (α) at the upper left of FIG. 14, "A", "B", "C", and "D" are assumed as the types of texture pattern for the disease corresponding to the disease cause (α).

Meanwhile, as can be seen from the lookup table corresponding to the disease cause (β) at the lower left of FIG. 14, "A", "B", "E", and "F" are assumed as the types of texture pattern for the disease corresponding to the disease cause (β).

Further, as can be seen from the lookup table corresponding to the disease cause (γ) at the upper right of FIG. 14, "A", "B", "H", and "J" are assumed as the types of texture pattern for the disease corresponding to the disease cause (γ).

Furthermore, as can be seen from the lookup table corresponding to the disease cause (δ) at the lower right of FIG. 14, "A", "B", "K", and "F" are assumed as the types of texture pattern for the disease corresponding to the disease cause (δ).

It is considered that the type of texture pattern to be assumed changes depending on the type of disease cause. Thus, in the case of estimating the change direction and rate of change in disease state from the change in type of texture pattern, it is preferred to consider the type of the disease cause.

The medical image processing apparatus 100 according to the second embodiment selects the lookup table corresponding to the disease cause designated by a user such as a doctor from among the previously stored lookup tables corresponding to the respective disease causes, and refers to the selected lookup table so as to estimate the change direction of the disease state of the object. As a result, the medical image processing apparatus 100 can estimate the change direction of the disease state with high accuracy, which contributes to a reliable diagnosis.

Modification of Second Embodiment

Figure 15:
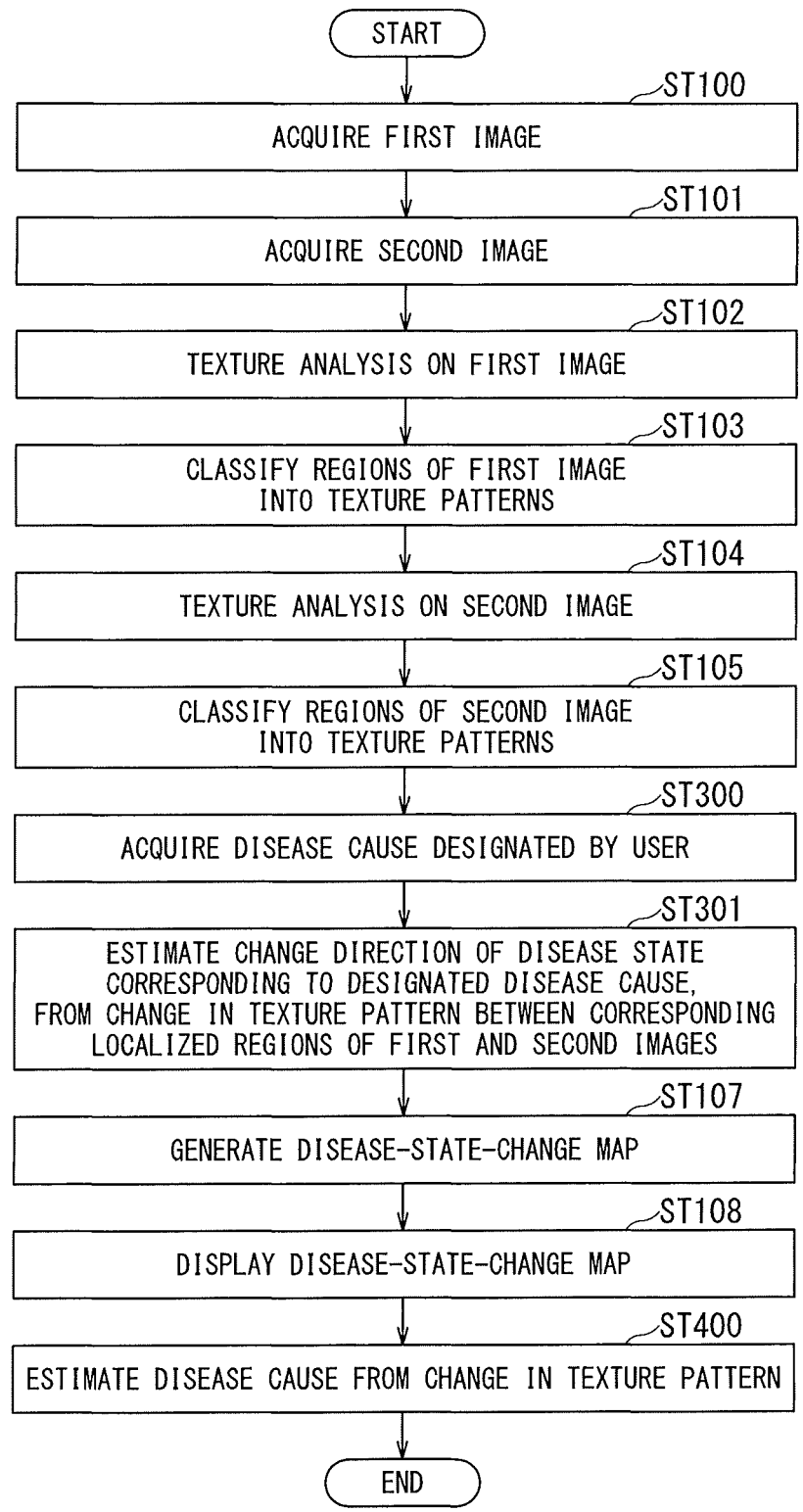
FIG. 15 is a flowchart illustrating processing performed by a medical image processing apparatus according to a modification of the second embodiment.

FIG. 15 is a flowchart illustrating processing performed by the medical image processing apparatus 100 according to a modification of the second embodiment. In the operation of the modification of the second embodiment, the processing of the step ST400 is further added to the entire processing of the second embodiment shown in the flowchart of FIG. 13. In the step ST400, the disease cause is estimated from the change in type of texture pattern. Note that the step ST300 in the flowchart in FIG. 15 may be omitted for the modification of the second embodiment.

Figure 16:
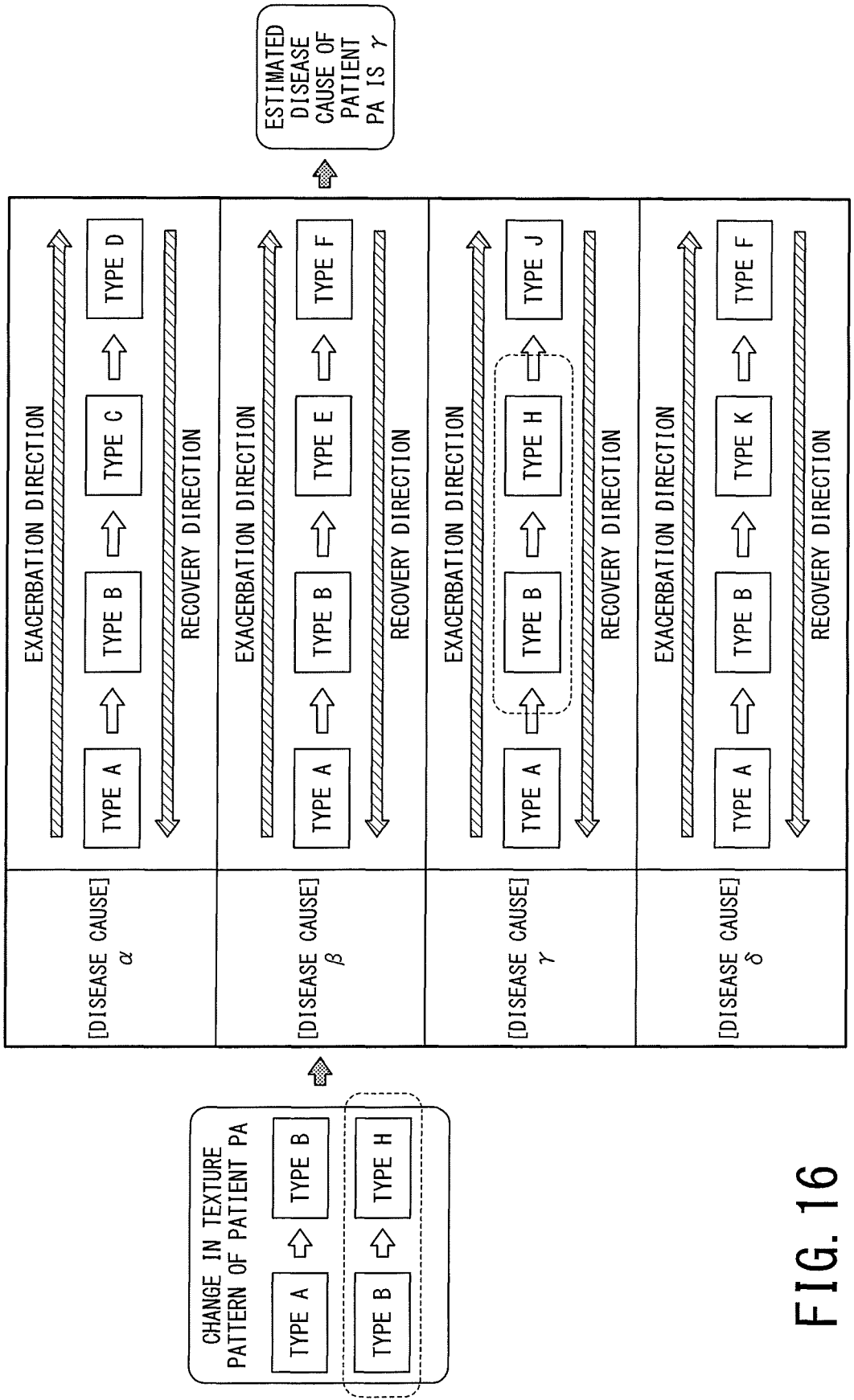
FIG. 16 is a schematic diagram illustrating the processing concept of estimating the disease cause from change in type of texture pattern.

FIG. 16 is a schematic diagram illustrating the processing concept of the step ST400. The central part of FIG. 16 illustrates a lookup table for estimating the disease cause. This lookup table is substantially the same as the four lookup tables shown in FIG. 14 and is compatible with the four lookup tables shown in FIG. 14.

As described above, the types of texture pattern that may change with disease progression differs depending on the disease cause in many cases. Thus, all the types of texture pattern that may change with disease progression are not necessarily identical as a whole. For example, as shown in the lookup table for estimating the disease cause in FIG. 16, although the change in texture pattern from the type "A" to "B" can occur commonly in the four disease causes (α), (β), (γ), and (δ), the change in texture patter from the type "B" to "H" can be caused only by the disease cause (γ).

In the modification of the second embodiment, the disease cause is estimated from the change direction of the texture pattern used in the processing of the step ST301 and the lookup table for estimating the disease cause. For example, as shown in the left part of FIG. 16, it is assumed that the texture pattern of the object (for example, patient PA) changes from the type "A" to "B" in one local region and from the type "B" to "H" in another local region. In this case, in the processing of the step ST400, it is estimated that the disease cause of the patient PA is the disease cause (γ).

In the modification of the second embodiment, the disease cause can be estimated from the change in type of texture pattern, and thus the medical image processing apparatus 100 can provide the user with more useful information for diagnosis.

Although several lookup tables are illustrated in FIG. 8, FIG. 11, FIG. 14, and FIG. 16, the medical image processing apparatus 100 is configured such that a user can generate, edit, and change the contents of these lookup tables.

Other Embodiments

So far, a description has been mainly given of embodiments in which the texture analysis is performed on the basis of the pixel values of the respective regions of the images (for example, the first and second images), and the respective regions are individually classified into one of the types of texture pattern. However, embodiments of the present invention are not limited to such an aspect.

For example, the present invention includes an embodiment in which (a) the tissue property of the object is classified into tissue-property classes by analyzing the tissue property on the basis of the pixel values of the respective regions of the plurality of images of the object, (b) the classified tissue-property classes are assigned to the respective regions of the plurality of images, and (c) change in disease state of the objects is estimated from change in tissue-property classes in respectively corresponding regions of the plurality of the images.

For example, analysis of tissue property of an object may include a TIC (Time-Intensity Curve) analysis (for example, analysis of temporal change in concentration of contrast agent), besides the above-described texture analysis. In the embodiment with the TIC analysis, the TIC curve obtained from the analysis result is classified into a plurality of types (i.e., tissue-property classes), and the change in disease state of the object is estimated from the change in type of the TIC curve. For example, when contrast-enhanced CT imaging is performed on an object with hepatocellular carcinoma in the normal liver, the curve rising of the early phase (i.e., arterial phase) is quicker than the TIC curve of normal tissues, and in the later phase (i.e., equilibrium phase), the curve is washed out and the curve falls. When the processing circuitry 20 classifies tissues into patterns (i.e., tissue-property classes) on the basis of the rate and/or timing of the rising and falling, the processing circuitry 20 can estimate the transition as to whether each tissue is getting exacerbated (i.e., approaches the cancer pattern from the normal tissue) or is recovering.

The analysis of tissue property of an object further includes analysis of luminance values in a region of an image of the object. In this embodiment, for example, a histogram of the luminance value is calculated by analyzing the luminance value and the shape of the histogram is classified into a plurality of types. For example, the shape of the histogram is classified into a plurality of types by using parameters such as kurtosis representing the sharpness of the peak of the histogram shape, the number of peaks in the histogram, and the luminance value corresponding to the peak of the histogram, and then the change in type of the shape of the histogram is used for estimating the change in disease state of the object. For example, when CT imaging is performed on an object having a pulmonary nodule, the region of the pulmonary nodule differs from normal regions in tissue density and thus differs from the normal regions in luminance value distribution (i.e., histogram) in CT imaging. In the case of the above-described pulmonary nodule, the proportion of the low density part decreases while the proportion of the high density part increases as compared with the normal tissues. By classifying the tissues into patterns (i.e., tissue-property classes) on the basis of the shape of the histogram, the processing circuitry 20 can estimate the change as to whether each tissue approaches from a normal tissue to a pulmonary nodule pattern (i.e., is getting exacerbated).

The analysis of tissue property of an object further includes analysis of a plurality of types of index values in a region of an image of the object. The plurality of types of index value are, for example, a luminance value in the region and a functional index value. The functional index value is, for example, an index value indicating the function of a tissue obtained from wall motion analysis or from cardiac nuclear medicine examination such as myocardial scintigraphy. In this embodiment, for example, the target region is classified into a plurality of groups on the basis of two values including the luminance value and the functional index value. For example, a group having a high luminance value and a high functional index value is classified into "the group 1", a group having a high luminance value and a low functional index value is classified into "the group 2", and a group having a low luminance value and a low functional index value is classified into "the group 3". In this case, change in disease state of the object is estimated from the change in classified group.

According to at least one embodiment described above, the change in disease state in the local region of the tissue can be readily grasped from the medical image.

The respective functions 21 to 25 illustrated in FIG. 2 are assumed to be implemented by one medical image processing apparatus 100 in each embodiment and modification described above. However, embodiments of the present invention are not limited to such an aspect. For example, the respective functions 21 to 25 illustrated in FIG. 2 may be implemented as distributed processing by a medical image processing system (not shown) in which a plurality of medical image processing apparatuses 100 are interconnected via a network. For example, a medical image processing system may be configured by the first and second medical image processing apparatuses 100A and 100B such that among the functions 21 to 25 shown in FIG. 2, a part of the functions are implemented by the first medical image processing apparatus 100A and the remaining functions are implemented by the second medical image processing apparatus 100B. Since each of the medical image processing apparatuses (100A and 100B) in the medical image processing system is interconnected via the network, the respective medical image processing apparatuses (100A and 100B) may be installed in different places.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
a memory configured to store a predetermined program; and
processing circuitry configured, by executing the predetermined program, to
acquire a plurality of images that are obtained by imaging a same object and are different in imaging time,
classify respective regions of the plurality of images into a plurality of texture patterns by performing texture analysis based on pixel values of the respective regions of the plurality of images,
assign the classified texture patterns to the respective regions of the plurality of the images, and
estimate change in disease state of the object from change in the texture patterns in respectively corresponding regions of the plurality of the images, wherein
the plurality of images are images of a lung field of the object, and
the plurality of texture patterns include at least one of a ground-glass opacities pattern, a reticular and linear opacities pattern, a nodular opacities pattern, a honeycombing pattern, and a consolidation pattern.

2. The medical image processing apparatus according to claim 1, wherein the processing circuitry is further configured to
estimate change in disease state for each of the corresponding regions, and
generate a map image by determining respective pixel values of the map image in such a manner that change in disease state is distinguishably depicted for each of the corresponding regions in any one of the plurality of images.

3. The medical image processing apparatus according to claim 1,
wherein the processing circuitry is configured to estimate the change in disease state and rate of the change in disease state in the respectively corresponding regions of the plurality of images, based on change in the texture patterns in the respectively corresponding regions of the plurality of images.

4. The medical image processing apparatus according to claim 1,
wherein the processing circuitry is configured to
acquire a first image and a second image, the first image being imaged at a first date and time, and the second image being imaged at a second date and time after the first date and time,
classify respective regions of the first image and the second image into the plurality of texture patterns, and
estimate whether a change direction of the disease state in local regions of the object is recovery, exacerbation, or no change, by using change in the texture patterns in respectively corresponding local regions of the first image and the second image.

5. The medical image processing apparatus according to claim 4,
wherein the processing circuitry is configured to estimate the change direction of the disease state for every pixel or for every pixel group consisting of two or more pixels.

6. The medical image processing apparatus according to claim 4, further comprising a display,
wherein the processing circuitry is configured to
generate a disease-state-change map in which the change direction of the disease state is depicted for every pixel or for every pixel group consisting of two or more pixels, and
cause the display to display the disease-state-change map.

7. The medical image processing apparatus according to claim 6,
wherein the processing circuitry is configured to generate the disease-state-change map in such a manner that the disease state is distinguishably depicted for every pixel or for every pixel group, with different manners including at least one of different chromatic colors, different grayscale, different numbers, and different signs.

8. The medical image processing apparatus according to claim 4, wherein:
the memory is configured to further store a lookup table in which types of the texture patterns are associated with degree of progression of the disease state; and
the processing circuitry is configured to estimate the change direction of the disease state by referring to the lookup table.

9. The medical image processing apparatus according to claim 8,
wherein the processing circuitry is configured to further estimate at least one of recovery rate in a recovery direction and exacerbation rate in an exacerbation direction by referring to the lookup table.

10. The medical image processing apparatus according to claim 8, wherein:
the memory is configured to further store lookup tables respectively corresponding to different disease causes, each of the lookup tables being a lookup table in which types of the texture patterns are associated with degree of progression of the disease state; and
the processing circuitry is configured to
estimate the change direction of the disease state based on one of the lookup tables corresponding to a disease designated by a user.

11. The medical image processing apparatus according to claim 10,
wherein the processing circuitry is configured to further estimate a disease cause of the object from change in the texture patterns in respectively corresponding local regions of the first image and the second image, based on the lookup tables respectively corresponding to different disease causes.

12. The medical image processing apparatus according to claim 8,
wherein the processing circuitry is configured to update contents of the lookup table stored in the memory through user operation.

13. A medical image processing system comprising:
processing circuitry configured to
- acquire a plurality of images that are obtained by imaging a same object and are different in imaging time,
- classify respective regions of the plurality of images into a plurality of texture patterns by performing texture analysis based on pixel values of the respective regions of the plurality of images,
- assign the classified texture patterns to the respective regions of the plurality of the images, and
- estimate change in disease state of the object from change in the texture patterns in respectively corresponding regions of the plurality of the images, wherein the plurality of images are images of a lung field of the object, and the plurality of texture patterns include at least one of a ground-glass opacities pattern, a reticular and linear opacities pattern, a nodular opacities pattern, a honeycombing pattern, and a consolidation pattern.

14. A medical image processing method comprising:
- acquiring a plurality of images that are obtained by imaging a same object and are different in imaging time;
- classifying respective regions of the plurality of images into a plurality of texture patterns by performing texture analysis based on pixel values of the respective regions of the plurality of images;
- assigning the classified texture patterns to the respective regions of the plurality of images; and
- estimating change in disease state of the object from change in the texture patterns in respectively corresponding regions of the plurality of images, wherein the plurality of images are images of a lung field of the object, and the plurality of texture patterns include at least one of a ground-glass opacities pattern, a reticular and linear opacities pattern, a nodular opacities pattern, a honeycombing pattern, and a consolidation pattern.

\* \* \* \* \*